United States Patent [19]

Hamazaki et al.

[11] 4,145,444

[45] * Mar. 20, 1979

[54] ANTI-INFLAMMATORY AGENT OF BENZOYL DERIVATIVE

[75] Inventors: Yasuhiko Hamazaki, Yachiyo; Shozo Kawabata, Saitama; Toshiyuki Yamamoto, Tokyo; Yasuo Shiraishi, Tokyo; Akira Ueno, Tokyo, all of Japan

[73] Assignee: Kaken Chemical Co., Ltd., Tokyo, Japan

[*] Notice: The portion of the term of this patent subsequent to Nov. 7, 1995, has been disclaimed.

[21] Appl. No.: 856,919

[22] Filed: Dec. 2, 1977

Related U.S. Application Data

[62] Division of Ser. No. 755,069, Dec. 28, 1976.

[51] Int. Cl.$^2$ .......................... C07C 49/76; A01N 9/12
[52] U.S. Cl. ..................................... 424/331; 260/591; 260/590 D
[58] Field of Search .......................... 424/331; 260/591

[56] References Cited

U.S. PATENT DOCUMENTS

| | | | |
|---|---|---|---|
| 4,027,040 | 5/1977 | Deroedt et al. | 424/331 |
| 4,062,978 | 12/1977 | Cole et al. | 424/331 |

OTHER PUBLICATIONS

Tsukervanik et al., Chem. Abst., vol. 75, #110011 (1971).
Takahashi et al., Chem. Abst., vol. 55, #26944L (1961).

*Primary Examiner*—James O. Thomas, Jr.
*Assistant Examiner*—James H. Reamer
*Attorney, Agent, or Firm*—Oblon, Fisher, Spivak, McClelland & Maier

[57] ABSTRACT

Anti-inflammatory agent comprises an active ingredient of benzoyl derivative having the formula

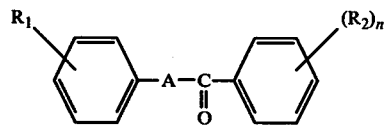

wherein
$R_1$ represents hydrogen, hydroxy, $C_{1-8}$ alkyl or $C_{1-8}$ alkoxy,
$R_2$ represents hydrogen, halogen, hydroxy, vinyl, $C_{1-8}$ alkyl or $C_{1-8}$ alkoxy,
A represents carbonyl, methylene or a single bond, and
n is an integer of 1 to 4.

1 Claim, No Drawings

ANTI-INFLAMMATORY AGENT OF BENZOYL DERIVATIVE

This is a division of application Ser. No. 755,069, filed Dec. 28, 1976.

BACKGROUND OF THE INVENTION

1. Field of the Invention

The present invention relates to anti-inflammatory agent which comprises an active ingredient of non-carboxylic benzoyl derivative.

2. Description of the Prior Arts

It has been known to use Aspirine, Oxyphenyl butazone, Indomethacin, Phenyl butazone, Ketophenyl butazone, Azapropazone, Mephanamic acid, Ibufenac, Benzydamine, Aminophiline as non-steroid anti-inflammatory agent.

These medicines cause side-effects, gastroenteric disorder, headache, etc.

The inventors have studied various compound and have found that the specific benzoyl compounds which do not belong to classes of the known compounds in chemical formulae had excellent effects as anti-inflammatory agents and analgesics and also had thrombosis inhibiting effect.

SUMMARY OF THE INVENTION

It is an object of the present invention to provide novel type anti-inflammatory agent and anti-thrombosis agent which does not cause side-effect.

Another object of the invention is to produce novel type anti-inflammatory agent.

The objects of the present invention have been attained by providing anti-inflammatory agent which comprises an active ingredient of non-carboxylic benzoyl derivative having the formula

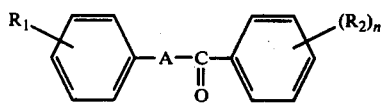

(I)

wherein
$R_1$ represents hydrogen, halogen, hydroxy, $C_{1-8}$ alkyl or $C_{1-8}$ alkoxy,
$R_2$ represents hydrogen, halogen, hydroxy, vinyl, $C_{1-8}$ alkyl or $C_{1-8}$ alkoxy,
A represents carbonyl, methyleen or a single bond, and 'n is an integer of 1 to 4.

It is preferable to be the active ingredient of benzoyl derivative having the formula

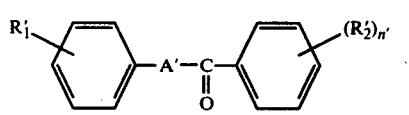

(I')

wherein $R'_1$ repreents hydrogen, halogen or $C_{1-8}$ alkyl,
$R'_2$ represents a substituent at ortho- or para-position which is hydrogen, $C_{1-8}$ alkyl or $C_{1-8}$ alkoxy,
A' represents carbonyl, methylene or a single bond, and
n' is an integer of 1 to 3.

I is especially preferable to be the active ingredient of

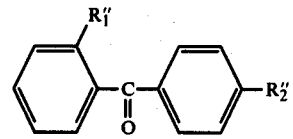

(I'')

wherein $R''_1$ represents hydrogen or halogen, and
$R''_2$ represents hydrogen, $C_{3-8}$ alkyl or $C_{1-8}$ alkoxy, especially

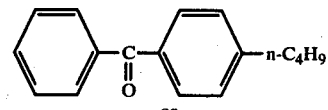

or

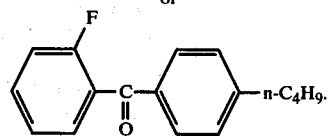

DETAILED DESCRIPTION OF THE PREFERRED EMBODIMENTS

The benzoyl derivatives used in the invention do not cause side-effect of gastroenteric disorder and had low toxicity and neutral compounds as different from the conventional ones.

For example, the benzoyl derivatives having the formula

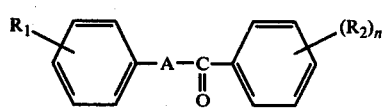

(I)

wherein $R_1$, $R_2$, A and n are defined above; are produced by reacting a compound having the formula

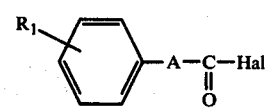

(II)

wherein $R_1$ and A are defined above and Hal represents a halogen atom with a compound having the formula

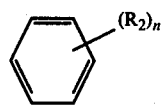

(III)

wherein $R_2$ and n are defined above,
in the presence of a catalyst and when A is —$CH_2$—, A can be converted to —CO— by reacting an oxidizing agent with the product.

The process for producing the benzoyl derivatives will be described in detail.

In the production of the compound I wherein A is a single bond or methylene group, the compound I is produced by reacting the compound II wherein A is a single bond or methylene group with the compound III in the presence of a catalyst.

Suitable catalysts include anhydrous aluminum chloride, anhydrous zinc chloride, anhydrous stannic chloride and other catalysts for these reactions.

Suitable organic solvents such as carbon disulfide, dichloromethane, dichloroethane can be used in the reaction.

The reaction is usually completed at 25° to 75° C. with stirring for 3 to 20 hours.

After the reaction, the solvent is distilled off and water is added to the residue and the product is extracted with benzene and the solution was washed with a caustic alkali solution, and then with water and dried. The solvent is distilled off to obtain a crude object product (ketone). The purification of the product is carried out by a distillation under a reduced pressure or a recrystallization or the other conventional method.

In the production of the compound I wherein A is keto group, the reaction is carried out by using the compound I wherein A is methylene group in the presence of an oxidizing agent such as selenium oxide. In the reaction, suitable solvent such as dioxane, water, ethanol or a mixture thereof can be used. The reaction is usually completed at 110° to 150° C. for 5 to 90 hours.

After the reaction, the precipitate is filtered and the solvent is distilled off under a reduced pressure from the filtrate.

Water is added to the residue and the product is extracted with chloroform. The chloroform solution is dried and the solvent is distilled off to obtain the crude object compound (benzyl).

The purification can be carried out by the conventional method.

The anti-inflammatory agent of the invention can be applied by various manners such as oral dose, intravenous injection, intramuscular injection and embrocation.

The anti-inflammatory agent of the invention can be used in various forms such as tablet, capsule, injection, syrup, ointment and the other pharmaceutical compositions.

The active ingredients can be applied together with the other anti-inflammatory agent, analgesics, thrombus dissolving agent, thormbus formation inhibiting agent, antibiotics, etc.

The dose of the benzoyl derivative (I) is dependent upon the kinds of the object diseases and is usually 0.5 to 1000 mg/kg/day.

The benzoyl derivatives (I) had various pharmacological effects as shown in the following tablets. As the anti-inflammatory effect, 2-fluorobenzophenone, 4-n-butyl benzophenone, 4-n-butyl-2'-fluorobenzophenone, 4-n-amyl-2-fluorobenzophenone and 2'-fluoro-2,4,6-trimethyl benzophenone have especially high inhibition rate ($ED_{50}$).

The followings are typical examples of novel compounds of benzoyl derivatives of the invention:

2-Fluoro-4'-n-propyl-benzophenone
2-Fluoro-4'-n-butyl-benzophenone
2-Fluoro-4'-n-amyl-benzophenone
2-Fluoro-4'-methoxy-benzophenone
2-Fluoro-4'-sec.butyl-benzophenone
2-Fluoro-4'-sec.amyl-benzophenone
4-Fluoro-4'-n-butyl-benzophenone
2-Fluoro-2',4',6'-trimethyl-benzophenone
2-Chloro-4'-n-butyl-benzophenone
2-Bromo-4'-n-amyl-benzophenone
2-Bromo-4'-n-octyl-benzophenone
2-Fluoro-4'-iso-propyl-benzophenone
2-Iodo-4'-n-amyl-benzophenone
2-Methyl-4'-n-butyl-benzophenone.

EXAMPLE 1

A 2.8 g (0.02 mole) of benzoic acid chloride was dissolved in 30 ml of carbon disulfide and then, 4.0 g (0.03 mole) of anhydrous aluminum chloride was added to the solution. A 2.68 g (0.02 mole) of n-butyl benzene was further added to the mixture with stirring, and the reaction was carried out at room temperature for 18 hours. Carbon disulfide was distilled off from the reaction mixture and water was added and the reaction product was extracted with benzene. The benzene phase was separated and washed with 1N-NaOH and with water and was dried with anhydrous sodium sulfate.

The solvent was distilled off to obtain a pale yellow oily product. The oily product was distilled under a reduced pressure to obtain 4.6 g of 4-n-butyl benzophenone having a boiling point of 184° to 188° C./6 mmHg. (yield of 96.8%).

EXAMPLE 2

A 3.16 g (0.02 mole) of 2-fluoro benzoic acid chloride was dissolved in 30 ml of carbon disulfide and then, 4.0 g (0.03 mole) of anhydrous aluminum chloride was added to the solution.

A 2.68 g (0.02 mole) of n-butyl benzene was further added to the mixture with stirring, and the reaction was carried out at room temperature for 18 hours.

In accordance with the process of Example 1, the reaction mixture was treated to obtain 3.2 g of 4-n-butyl-2'-fluorobenzophenone having a boiling point of 180° to 190° C./5 mmHg. (yield of 62.5%).

EXAMPLE 3

A 21.4 g (0.16 mole) of n-butyl benzene and 25.0 g (0.162 mole) of phenyl acetic acid chloride were added to 100 ml of carbon disulfide, and 22.0 g (0.165 mole) of anhydrous aluminum chloride was further added to them with stirring and the reaction was carried out at room temperature for 15 hours.

In accordance with the process of Example 1, the reaction mixture was treated and the product was recrystallized from ethanol to obtain 39.0 g of 4-n-butyl-α-phenyl acetophenone having a melting point of 53° to 55° C. which had the formula

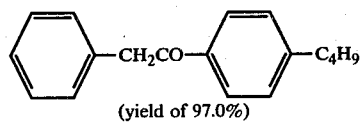

(yield of 97.0%)

EXAMPLE 4

A 19.7 g (0.78 mole) of 4-n-butyl-α-phenyl acetophenone of Example 3 was dissolved in 200 ml of a mixture of dioxane 5; water 1, and 9.0 g (0.81 mole) of selenium dioxide was added to the solution and the mixture was heated under refluxing to react them for 90 hours. The resulting black precipitate was filtered off and the solvent was distilled off under a reduced pressure from the filtrate.

The residue was dissolved in chloroform and the solution was washed with water and was dried.

The solvent was distilled off under a reduced pressure and the resulting oily product was distilled under a reduced pressure to obtain 18.7 g of 4-n-butyl benzyl having a boiling point of 240° to 242° C./5 mmHg which had the formula

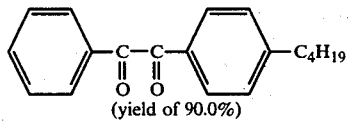

(yield of 90.0%)

EXAMPLE 5

A 3.17 g (0.02 mole) of 2-fluorobenzoic acid chloride was dissolved in 30 ml of carbon bisulfide and then, 3.99 g (0.03 mole) of anhydrous aluminum chloride was added to the solution.

A 2.68 g (0.02 mole) of sec-butyl benzene was further added to the mixture with stirring and the reaction was carried out at room temperature for 18 hours. Carbon bisulfide was distilled off from the reaction mixture and water was added and the reaction product was extracted with benzene. The benzene phase was separated washed with 1N-NaOH and with water and was dried with anhydrous sodium sulfate. The solvent was distilled off to obtain a pale yellow oily product. The oily product was distilled under a reduced pressure to obtain 3.9 g of 4-sec-butyl-2'-fluorobenzophenone having a boiling point of 152° to 160° C./5 mmHg. (yield of 76.4%).

EXAMPLE 6

A 3.17 g (0.02 mole) of 2-fluorobenzoic acid chloride was dissolved in 30 ml of carbon disulfide and then, 3.99 g (0.03 mole) of anhydrous aluminum chloride was added to the solution. A 2.96 g (0.02 mole) of sec-amyl benzene was further added to the mixture with stirring and the reaction was carried out at room temperature for 18 hours.

In accordance with the process of Example 1, the reaction mixture was treated to obtain 4.0 g of 4-sec-amyl-2'-fluorobenzophenone having a boiling point of 150° to 157° C./4 mmHg. (yield of 74%).

The properties of the compounds produced in Examples 1 to 6 and the other compounds produced by the same manner are shown. The physical properties are shown in Table 1 and the pharmacological effects are shown in Table 2.

In the column for melting points and boiling points in Table 1, the symbol * means the melting point. In the column for IR in Table 1, the symbol * means $v_{max}^{nujol}$ cm$^{-1}$.

In Table 2, the pharmacological effects and toxicity were measured by the following tests.

Anti-inflammatory effect

The edema inhibition rates (%) of the samples of the invention were measured in accordance with acute carragheenin edema method described in Nippon Yakurigaku Zatsushi Vol. 56, Page 575 in 1960.

The edema was induced by subcutaneous injection of 1% carragheenin suspension in saline to the hind paws of male rats weighting 150 to 180 g. Each sample was orally given at the dosage of 100 mg/kg just before the inoculation of carragheenin.

In Table 2, the values shown in brackets show the 50% inhibition rae ED$_{50}$ (mg/kg).

Analgesic effect

In accordance with the method described in Federation Proceedings Vol. 18, Page 412 in 1959, percentage diminition of times of painful stretchings (%) following the intraperitorineal injection of 0.7% acetic acid solution in male mice (weight of 20 to 25 g) were counted.

Each sample was orally administered in the dosage of 100 mg/kg before injection of acetic acid.

Blood platelet aggregation inhibiting effect

Male rabbits (Japan original white strain 3.3 to 3.6 kg) were anesthetized with Thiopental sodium and blood was sampled from the carotid artery.

In order to prevent coaggulation of the blood, 10% by volume of 3.8% sodium citrate aqueous solution was added to the blood.

The light transmittances were adjusted to 0% with PRP (supernatant platelet rich plasma separated by centrifugation at 1600 rpm from blood) and to 100% with PPP (supernatant platelet poor plasma separated by centrifugation at 3000 rpm from blood) by using the Blood platelet aggregometer (Model EEL-169, Electroserum Co. England). The platelet aggregation was measured in accordance with the test method described in Federation Preceedings Vol. 26, Page 115 in 1967, using collagen as an aggregation inducer.

The percent inhibition of platelet aggregation was given as the difference in the platelet aggregation rate % between the sample (concentration: $10^{-4}$ mole) and control (saline), with the rate of control adjusted to 100%.

Acute toxicity

Each sample was dissolved in olive oil or dispersed in 1% Tween 20 aqueous solution. The test was carried out by the oral dose in male mice having a weight of 22 to 25 g.

Ten animals were used at each of three or more dosage levels. General appearances and behaviors were observed for 7 days after treatment, and LD$_{50}$ was calculated on the basis of mice that succumbed within 72 hours using Van Der Warden method.

Inhibiting effect on thrombosis

The inhibiting effects of the samples of the invention on thrombosis were tested by the following test method.

SD type male rates (360 to 580 g) were anesthetized by the intraperitoneal injection of Thiopental sodium (67 mg/kg). In accordance with the technique described in *Proceeding Society o Experimental Biological Medicine* Vol. 139, Pages 548 to 552 in 1972 by Hermann, the by-pass was formed between the left juglar vein and the right carotid artery with a polyethylene tube.

A 0.5 ml of 50 $\mu$/ml of the heparin physiological saline was added through the polyethylene tube before the first blood circulation. After the blood circulation for 15 minutes, the circulation was stopped in the middle of the tubing at artery side with a pinch cock.

Then, 0.2 ml of the heparin physiological saline was added to remove the blood coagulates on the tubing wall and another new polyethylene tubing filled with the heparin solution and containing a piece of new silk thread was attached between the venous and artery tubing ends.

The blood circulation was reestablished by opening the pinch cock. After 15 minutes, the wet weight of thrombus on the silk thread was similarly measured.

In the same manner, the third circulation was performed and wet weight of thrombus measured.

The amount of thrombus was given by the equation A.

$$\begin{pmatrix} \text{Wet weight of} \\ \text{silk thread} \\ \text{coated with} \\ \text{thrombus} \end{pmatrix} - \begin{pmatrix} \text{Wet weight of} \\ \text{silk thread} \\ \text{method only} \\ \text{with heparin} \end{pmatrix} = \begin{pmatrix} \text{Amount of} \\ \text{thrombosis} \end{pmatrix} \quad (A).$$

Each sample was suspended in an aqueous solution of sodium carboxymethyl cellulose and the oral dose of the suspension (100 mg/kg) was performed at 5 hours before the first blood circulation.

The amount of thrombus after the oral dose of the sample was calculated in the same manner as that of control circulations.

The thrombosis inhibition rate was given by the equation B.

$$\begin{pmatrix} \text{Thrombosis inhibition} \\ \text{rate} \end{pmatrix} =$$

$$\frac{\begin{pmatrix} \text{Amount of} \\ \text{thrombus in} \\ \text{control} \end{pmatrix} - \begin{pmatrix} \text{Amount of throm-} \\ \text{bus after oral} \\ \text{dose of sample} \end{pmatrix}}{(\text{Amount of thrombus in control})} \times 100 \quad (B).$$

The test results are shown in Table 2.

| Composition 1: | |
|---|---|
| Active ingredient No. 8 | 100 g |
| Fine powdery silica (Solider 101) | 100 g |
| Crystalline cellulose | 645 g |
| Corn starch | 125 g |
| Magnesium stearate | 30 g |

The fine powdery silica was admixed with the same amount of the active ingredient No. 8, and the mixture was passed through a 32 mesh sieve.

The mixture was admixed with crystalline cellulose, corn starch and magnesium stearate and the components were uniformly mixed by passing through a 32 mesh sieve.

The mixture was treated by the tablet machine to form tablets having a diameter of 8 mm and a weight of 200 mg.

| Composition 2: | |
|---|---|
| Active ingredient No. 3 | 125 g |
| Lactose | 650 g |
| Crystalline cellulose | 100 g |
| Corn starch | 100 g |
| 3% hydroxypropyl cellulose aqueous solution | 500 ml |
| Magnesium stearate | 10 g |

The lactose, crystalline cellulose and corn starch were admixed with the active ingredient No. 3, and the mixture was passed through a 60 mesh sieve to uniformly mix the components. The mixture was charged in a kneader and 3% hydroxypropyl cellulose aqueous solution was added and the mixture was kneaded.

The mixture was granulated by passing through a 16 mesh sieve and was dried at 50° C. and then passed through a 16 mesh sieve to cause uniform particle sizes.

The granules were mixed with magnesium stearate and was treated by the tablet machine to form tablets having a diameter of 8 mm and a weight of 200 mg.

| Composition 3: | |
|---|---|
| Active ingredient No. 119 | 100 g |
| Fine powdery silica (Solider 101) | 100 g |
| Crystalline cellulose | 645 g |
| Corn starch | 125 g |
| Magnesium stearate | 30 g |

The fine powdery silica was admixed with the same amount of the active ingredient No. 119 and the mixture was passed through a 32 mesh sieve.

The mixture was admixed with crystalline cellulose, corn starch and magnesium stearate and the components were uniformly mixed by passing through a 32 mesh sieve.

The mixture was treated by the tablet machine to form tablets having a diameter of 8 mm and a weight of 200 mg.

| Composition 4: | |
|---|---|
| Active ingredient No. 136 | 125 g |
| Lactose | 650 g |
| Crystalline cellulose | 100 g |
| Corn starch | 100 g |
| 3% hydroxypropyl cellulose aqueous solution | 500 ml |
| Magnesium stearate | 10 g |

The active ingredient No. 136 was uniformly mixed with lactose, crystalline cellulose and corn starch by passing through a 60 mesh sieve.

The 3% hydroxypropyl cellulose aqueous solution was added to the mixture in a kneader and the mixture was granulated by passing through a 16 mesh sieve and was dried at 50° C. under air-flow. The dried granules were passed through a 16 mesh sieve to cause uniform particle sizes. The granules were mixed with magnesium stearate and was treated by the tablet machine to form tablets having a diameter of 8 mm and a weight of 200 mg.

Table 1

| Active ingredient No. | $R_1$ | $R_2$ | A | Biling point (° C/mmHg) or melting point (° C) | IR $(C=O)$ $\nu_{max}^{nujol}$ cm$^{-1}$ |
|---|---|---|---|---|---|
| 1 | 2-CH$_3$ | 2,4-diCH$_3$ | single bond | 155~160/3 | 1660 |
| 2 | " | 2,5-diCH$_3$ | " | 148–152/3 | 1655 |
| 3 | " | 2,4,6-triCH$_3$ | " | 111~112* | 1660* |
| 4 | 4-n-C$_6$H$_{13}$ | 2,4-diCH$_3$ | " | 203~5/4 | 1655 |
| 5 | " | 4-n-C$_4$H$_9$ | " | 228/3 | 1650 |

Table 1-continued

| Active ingredient No. | $R_1$ | $R_2$ | A | Boiling point (° C/mmHg) or melting point (° C) | IR $(C=O)$ $\nu_{max}^{nujol}$ cm$^{-1}$ |
|---|---|---|---|---|---|
| 6 | " | 4-n-$C_3H_7$ | " | 213~5/3 | 1650 |
| 7 | 2-F | " | " | 160~5/5 | 1660 |
| 8 | " | 4-n-$C_4H_9$ | " | 180~190/5 | 1660 |
| 9 | " | 4-n-$C_5H_{11}$ | " | 190~5/5 | 1660 |
| 10 | " | 2,4-di$CH_3$ | " | 150~5/5 | 1655 |
| 11 | " | 2,4,6-tri$CH_3$ | " | 155~160/5 | 1660 |
| 12 | H | 4-$OCH_3$ | C=O | 180~190/2 | 1660 |
| 13 | " | 2,4,6-tri$C_2H_5$ | single bond | 176.5~178/6.5 | 1665 |
| 14 | 4-Cl | 2,4,6-tri$CH_3$ | " | 65~7* | 1660* |
| 15 | H | 2-F | " | 190/29 | 1665 |
| 16 | " | 2,5-n-di$C_3H_7$ | " | 172~182/5 | 1665 |
| 17 | 4-$CH_3$ | 2,5-n-di$C_4H_9$ | " | 175~191/2.5 | 1660 |
| 18 | 4-$OCH_3$ | 4-n-$C_4H_9$ | " |  | 1645 |
| 19 | H | " | " | 184~188/6 | 1660 |
| 20 | " | 4-n-$C_3H_7$ | " | 161~167/3.5 | 1660 |
| 21 | " | 4-i-$C_3H_7$ | " | 143~4/2 | 1660 |
| 22 | " | 4-t-$C_4H_9$ | " | 141~144/1 | 1660 |
| 23 | " | 4-n-$C_5H_{11}$ | " | 164~167/2.5~3 | 1660 |
| 24 | " | 4-n-$C_6H_{13}$ | " | 185~190/3 | 1655 |
| 25 | " | 4-n-$C_7H_{15}$ | " | 173~175/2~2.5 | 1660 |
| 26 | " | 4-n-$C_8H_{17}$ | " | 185~190/3 | 1655 |
| 27 | " | H | " | 48~49.5* | 1660* |
| 28 | " | 4-$OCH_3$ | " | 58~60* | 1660 |
| 29 | " | 4-n-$C_4H_9$ | C=O | 240~242/5 | 1660 |
| 30 | " | 2,4,6-tri$CH_3$ | single bond | 131~133/1.5~2 | 1665 |
| 31 | " | 2,3,4-tri$CH_3$ | " | 145.5~148/2 | 1665 |
| 32 | " | 2,4,5-tri$CH_3$ | " | 152~154/3 | 1665 |
| 33 | 4-$CH_3$ | 4-$C_2H_5$ | " | 46~9* | 1645* |
| 34 | " | 4-n-$C_3H_7$ | " | 160~3/3 | 1650 |
| 35 | " | 4-n-$C_4H_9$ | " | 160~5/3 | 1655 |
| 36 | " | 4-n-$C_6H_{13}$ | " | 190~6/2 | 1650 |
| 37 | H | 2,4-di$CH_3$ | " | 120~122/1~1.5 | 1660 |
| 38 | " | 2,5-di$CH_3$ | " | 132~134.5/3 | 1665 |
| 39 | " | 4-n-$C_4H_9$ | $CH_2$ | 53~55* | 1670* |
| 40 | 2-$CH_3$ | " | single bond | 157~163/2 | 1665 |
| 41 | " | 4-n-$C_5H_{11}$ | " | 159~169/1 | 1665 |
| 42 | H | 4-n-$OC_4H_9$ | " | 27~29* | 1650* |
| 43 | 4-n-$C_4H_9$ | 4-n-$C_4H_9$ | " | 205~210/3.5 | 1650 |
| 44 | 2-Cl | 4-n-$C_4H_9$ | " | 200~5/5 | 1660 |
| 45 | 4-$OCH_3$ | 4-n-$C_5H_{11}$ | " |  | 1645 |
| 46 | 4-n-$C_4H_9$ | 4-F,2-$CH_3$ | " | 140~142/3 | 1650 |
| 47 | H | H | $CH_2$ | 55* | 1670* |
| 48 | " | 4-$CH_3$ | " | 104~106* | 1670* |
| 49 | H | 4-n-$C_3H_7$ | $CH_2$ | 53-54* | 1670* |
| 50 | " | 4-n-$C_{10}H_{21}$ | " | 50-52* | 1670* |
| 51 | " | 4-n-$C_{11}H_{23}$ | " | 51-53* | 1670* |
| 52 | " | 4-n-$C_{12}H_{25}$ | " | 55-58* | 1670* |
| 53 | " | H | C=O | 95* | 1660* |
| 54 | " | 4-$CH_3$ | " | 180/1 | 1660 |
| 55 | " | 4-$C_2H_5$ | " | 170/1 | 1660 |
| 56 | " | 4-n-$C_6H_{13}$ | " | 200-210/1 | 1660 |
| 57 | " | 4-$OCH_3$ | $CH_2$ | 66-68* | 1660* |
| 58 | " | 4-n-$OC_3H_7$ | " | 85-87* | 1670* |
| 59 | " | 4-n-$OC_5H_{11}$ | " | 62-65* | 1675* |
| 60 | 4-Cl | 4-$OCH_3$ | " | 118-119* | 1630* |
| 61 | " | 4-n-$OC_4H_9$ | " | 100-101* | 1630* |
| 62 | " | 4-n-$OC_6H_{13}$ | " | 88-89* | 1630* |
| 63 | " | 4-n-$C_3H_7$ | single bond | 77-78* | 1640* |
| 64 | " | 4-n-$C_4H_9$ | " | 62-53* | 1640* |
| 65 | H | 4-$CH_3$ | " | 45-47* | 1640* |
| 66 | " | 4-$C_2H_5$ | " | 133-134/2 | 1655 |
| 67 | " | 4-i-$C_4H_9$ | " | 170-172/4 | 1655 |
| 68 | " | 4-n-$C_{10}H_{21}$ | " | 205-210/2 | 1660 |
| 69 | " | 4-n-$C_{12}H_{25}$ | " | 215-219/2 | 1660 |
| 70 | " | 4-n-$C_9H_{19}$ | " | 187-194/25-3 | 1665 |
| 71 | H | 4-n-$C_{11}H_{23}$ | " | 19914 209/2.5 | 1660 |
| 72 | " | 3,4-di$CH_3$ | " | 139-144/1 | 1660 |
| 73 | " | 4-cyclo$C_6H_{13}$ | " | 170-182/1 | 1660 |
| 74 | " | 2,4-di$OCH_3$ | " | 87-88* | 1660* |
| 75 | " | 2,5-di$OCH_3$ | " | 50-52* | 1660* |
| 76 | " | 2,4,6-tri$OCH_3$ | " | 178-179* | 1660* |
| 77 | " | 2,5-di-n-$C_4H_9$ | " | 158-169/2 | 1660 |
| 78 | " | 2,3,5,6-tetra$CH_3$ | " | 116-118* | 1670* |
| 79 | " | 2,3,4,6-tetra$CH_3$ | " | 171-172/5.5 | 1670 |
| 80 | " | 2,5-di$C_2H_5$ | " | 161-165/4 | 1665 |
| 81 | " | 4-$OC_2H_5$ | " | 38-39* | 1645* |
| 82 | " | 4-$CH=CH_2$ | " | oily | 1660 |
| 83 | 4-$CH_3$ | 4-$CH_3$ | " | 91-93* | 1645* |
| 84 | " | 4-n-$C_5H_{11}$ | " | 170-175/2 | 1655 |
| 85 | " | 4-n-$C_7H_{15}$ | " | 195-203/3 | 1650 |
| 86 | " | 2,4,6-tri $CH_3$ | " | 148-149/2.5 | 1665 |
| 87 | 3-$CH_3$ | 4-n-$C_3H_7$ | " | 162-165/4 | 1650 |
| 88 | " | 4-n-$C_4H_9$ | " | 165-170/3 | 1650 |
| 89 | " | 4-n-$C_5H_{11}$ | " | 175-180/3 | 1650 |
| 90 | 2-$CH_3$ | 4-n-$C_3H_7$ | " | 140-147/1.5 | 1665 |

Table 1-continued

| Active ingredient No. | $R_1$ | $R_2$ | A | Boiling point (° C/mmHg) or melting point (° C) | IR $\nu_{max}^{nujol}$ $(C=O)$ cm$^{-1}$ |
|---|---|---|---|---|---|
| 91 | " | 2,3,5,6-tetraCH$_3$ | " | 105–107* | 1660* |
| 92 | 4-OCH$_3$ | 4-OCH$_3$ | " | 141–142* | 1640* |
| 93 | 4-OCH$_3$ | 4-n-C$_3$H$_7$ | " | oily | 1645 |
| 94 | 4-n-OC$_4$H$_9$ | 2,4,6-triCH$_3$ | " | 190–194/3 | 1660 |
| 95 | " | 4-n-C$_4$H$_9$ | " | 190–210/3 | 1650 |
| 96 | 4-n-C$_3$H$_7$ | 2,4-diCH$_3$ | " | 185/4 | 1655 |
| 97 | " | 2,4,6-triCH$_3$ | " | 183–185/4 | 1650 |
| 98 | " | 4-n-C$_4$H$_9$ | " | 207–210/3.5 | 1655 |
| 99 | " | 4-n-C$_5$H$_{11}$ | " | 217–220/4 | 1650 |
| 100 | 4-n-C$_4$H$_9$ | 4-n-C$_7$H$_{15}$ | " | oily | 1650 |
| 101 | " | 4-n-C$_8$H$_{17}$ | " | " | 1650 |
| 102 | " | 4-n-C$_9$H$_{19}$ | " | 1 | 1650 |
| 103 | 4-n-C$_6$H$_{13}$ | 2,4,6-triCH$_3$ | " | 205–210/4 | 1660 |
| 104 | 4-OH | 4-n-C$_3$H$_7$ | " | | 1630 |
| 105 | " | 4-n-C$_5$H$_{11}$ | " | | 1630 |
| 106 | 4-C$_2$H$_5$ | 4-C$_2$H$_5$ | " | 47* | 1650* |
| 107 | 4-OCH$_3$ | 4-C$_2$H$_5$ | " | 41–43* | 1640* |
| 108 | 4-OH | 2,4,6-triCH$_3$ | " | | 1630 |
| 109 | H | 4-OH | " | 132–135* | 1630* |
| 110 | 4-n-C$_3$H$_7$ | 4-n-C$_3$H$_7$ | " | 65–67* | 1650* |
| 111 | 4-n-C$_5$H$_{11}$ | 4-n-C$_5$H$_{11}$ | " | 220–222/4 | 1650 |
| 112 | 4-n-C$_2$H$_5$ | 4-n-C$_3$H$_7$ | " | | 1660 |
| 113 | H | | " | 146–147* | 1660* |

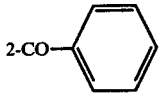

2-CO—⌬

| 114 | 4-F | 4-F | " | 102–105* | 1640* |
| 115 | 2-Cl | 4-F | " | 60–62* | 1660* |
| 116 | 2-F | 4-OCH$_3$ | " | 155–160/5 | 1660 |
| 117 | " | 4-i-C$_3$H$_7$ | " | 142–152/5 | 1655 |
| 118 | " | 4-i-C$_4$H$_9$ | " | 152–7/4 | 1660 |
| 119 | " | 4-s-C$_4$H$_9$ | " | 155–160/5 | 1660 |
| 120 | " | 4-t-C$_4$H$_9$ | " | 152–157/5 | 1655 |
| 121 | " | 4-s-C$_5$H$_{11}$ | " | 150–7/4 | 1660 |
| 122 | " | 4-t-C$_5$H$_{11}$ | " | 160–5/5 | 1665 |
| 123 | 3-F | 4-n-C$_4$H$_9$ | " | 182–7/5 | 1660 |
| 124 | " | 4-n-C$_5$H$_{11}$ | " | 185–195/5 | 1655 |
| 125 | " | 2,4,6-triCH$_3$ | " | oily | 1670 |
| 126 | " | 2,4-di-CH$_3$ | " | 150–3/5 | 1660 |
| 127 | 4-F | 4-n-C$_4$H$_9$ | " | 39–40* | 1645* |
| 128 | " | 4-n-C$_5$H$_{11}$ | " | 46–7* | 1645* |
| 129 | " | 4-n-C$_8$H$_{17}$ | " | 32–3* | 1645* |
| 130 | " | 2,4-diCH$_3$ | " | 149–152/5 | 1660 |
| 131 | " | 2,4,6-triCH$_3$ | " | 150–2/5 | 1670 |
| 132 | 2-Cl | 4-n-C$_3$H$_7$ | " | 188–190/5 | 1660 |
| 133 | " | 4-n-C$_5$H$_{11}$ | " | 200–4/5 | 1665 |
| 134 | " | 4-n-C$_8$H$_{17}$ | " | 235–7/5 | 1665 |
| 135 | " | 2,4-diCH$_3$ | " | 174–6/5 | 1660 |
| 136 | 4-Cl | 4-OCH$_3$ | " | 118–9* | 1630$^{N*}$ |
| 137 | " | 4-OC$_4$H$_9$ | " | 100–1* | 1630$^{N*}$ |
| 138 | " | 4-OC$_6$H$_{13}$ | " | 88–9* | 1630$^{N*}$ |
| 139 | 3-Cl | 4-n-C$_3$H$_7$ | " | 27–8* | 1670* |
| 140 | " | 4-n-C$_5$H$_{11}$ | " | 355–7* | 1660* |
| 141 | " | 4-n-C$_8$H$_{17}$ | " | oily | 1660 |
| 142 | 2-Br | 4-n-C$_3$H$_7$ | " | 39–40* | 1670* |
| 143 | " | 4-n-C$_4$H$_9$ | " | 203–210/5 | 1660 |
| 144 | " | 4-n-C$_5$H$_{11}$ | " | 210–215/5 | 1670 |
| 145 | " | 4-n-C$_8$H$_{17}$ | " | 240–3/4 | 1665 |
| 146 | " | 2,4-diCH$_3$ | " | 182–3/5 | 1660 |
| 147 | " | 2,4,6-triCH$_3$ | " | 113–4* | 1670* |
| 148 | 3-Br | 4-n-C$_8$H$_{17}$ | " | 240–5/6 | 1650 |
| 149 | " | 2,4-diCH$_3$ | " | 180–2/6 | 1650 |
| 150 | 4-Br | 4-n-C$_3$H$_7$ | " | 93–4* | 1640* |
| 151 | " | 4-n-C$_8$H$_{17}$ | " | 53–4* | 1640* |
| 152 | " | 2,4-diCH$_3$ | " | 180–5/6 | 1655 |
| 153 | " | 2,4,6-triCH$_3$ | " | 70–1* | 1660* |
| 154 | 2-I | 4-n-C$_3$H$_7$ | " | 190–7/5 | 1660 |
| 155 | " | 4-n-C$_4$H$_9$ | " | 202–9/4 | 1660 |
| 156 | " | 4-n-C$_5$H$_{11}$ | " | 207–218/4 | 1660 |
| 157 | " | 4-n-C$_8$H$_{17}$ | " | 215–220/4 | 1665 |
| 158 | 2-I | 2,4-diCH$_3$ | " | 192–7/5 | 1660 |
| 159 | " | 2,4,6-triCH$_3$ | " | 97–8* | 1665* |
| 160 | 3-I | 4-n-C$_4$H$_9$ | " | 45–7* | 1645* |
| 161 | " | 4-n-C$_8$H$_{17}$ | " | 215–20/4 | 1655 |
| 162 | " | 2,4-diCH$_3$ | " | 74–5* | 1655* |
| 163 | " | 2,4,6-triCH$_3$ | " | 85–6* | 1660* |
| 164 | 4-I | 4-n-C$_8$H$_{17}$ | " | 64–5* | 1640* |
| 165 | " | 2,4-diCH$_3$ | " | 200–5/7 | 1655 |
| 166 | " | 2,4,6-triCH$_3$ | " | 72–3* | 1665* |

In Table, the following references are shown for columns.

Table 2

Anti-inf. = edema inhibition rate (%) for anti-inflammatory effect;

Analgesic = percentage diminition of times of painful

Table 2-continued

Blood platelet agg. inh. = percentage inhibition of platelet aggregation for blood platelet aggregation inhibiting effect;

Thrombosis inh. = thrombosis inhibition rate for inhibiting effect on thrombosis.

stretching (%) for analgesic;

| Active ingredient No. | Anti-inf. (%) | Analgesic (%) | Blood platelet agg. inh. | Acute toxicity $LD_{50}$ (mg/kg) | Thrombosis inh. (%) |
|---|---|---|---|---|---|
| 1 | 36.2 (700) | 10.2 | 21.7 | 1000 | 28.5 |
| 2 | 36.8 | 13.5 | 19.5 | 1000 | 30.3 |
| 3 | 40.0 (290) | 11.3 | 17.3 | 1500 | 38.3 |
| 4 | 44.2 | 16.3 | 20.5 | 4000 | 15.9 |
| 5 | 46.3 | 12.1 | 15.3 | 5000 | 20.3 |
| 6 | 44.2 | 14.5 | 17.8 | 5000 | 15.9 |
| 7 | 55.6 (78) | 15.0 | 23.0 | 1500 | 24.6 |
| 8 | 82.6 (38) | 14.8 | 24.0 | 1500 | 38.0 |
| 9 | 74.6 (22) | 15.3 | 14.6 | 3000 | 25.3 |
| 10 | 47.5 (90) | 20.3 | 18.5 | 500 | 29.7 |
| 11 | 62.3 (22) | 13.9 | 16.5 | 500 | 42.9 |
| 12 | 43.9 | 10.2 | 20.1 | 10000 | 18.3 |
| 13 | 38.9 (>400) | 15.8 | 14.3 | 2000 | 20.5 |
| 14 | 37.3 (130) | 19.2 | 18.1 | 500 | 23.3 |
| 15 | 61.4 (65) | 18.5 | 23.2 | 4000 | 26.5 |
| 16 | 45.2 (140) | 12.4 | 8.6 | 1500 | 21.5 |
| 17 | 36.3 (180) | 10.3 | 17.3 | 2000 | 19.5 |
| 18 | 41.6 | 20.1 | 9.3 | 2000 | 24.2 |
| 19 | 63.4 (25) | 30.1 | 18.6 | 2400 | 7.9 |
| 20 | 42.7 | 17.3 | 36.6 | 2000 | 4.1 |
| 21 | 37.3 | 16.1 | 8.6 | 2000 | 5.4 |
| 22 | 36.4 | 8.2 | 9.5 | 2000 | 7.9 |
| 23 | 50.4 | 10.1 | 13.8 | 5000 | 22.3 |
| 24 | 37.6 | 47.7 | 10.5 | 6000 | 24.3 |
| 25 | 40.8 | 48.6 | 7.8 | 8000 | 22.1 |
| 26 | 47.2 | 35.9 | 3.1 | 10000 | 24.8 |
| 27 | 47.7 (120) | 13.2 | 25.7 | 3700 | 25.9 |
| 28 | 44.1 | 4.2 | 20.4 | >10000 | 7.3 |
| 29 | 44.7 (130) | 2.7 | 11.1 | 10000 | 15.3 |
| 30 | 64.7 (45) | 13.4 | 8.7 | 1500 | 44.8 |
| 31 | 35.4 | 9.5 | 18.2 | 1500 | 23.5 |
| 32 | 47.7 | 26.2 | 12.4 | 2000 | 25.0 |
| 33 | 43.9 | 15.5 | 20.5 | 3000 | 28.3 |
| 34 | 43.1 | 12.1 | 16.4 | 5000 | 24.5 |
| 35 | 48.5 | 17.8 | 11.3 | >10000 | 2.65 |
| 36 | 34.8 | 13.7 | 15.1 | >10000 | 28.1 |
| 37 | 39.6 | 9.8 | 17.4 | 1000 | 5.3 |
| 38 | 37.5 (170) | 18.0 | 20.9 | 1000 | 8.3 |
| 39 | 35.9 | 23.1 | 2.6 | >10000 | 15.9 |
| 40 | 58.1 (120) | 20.3 | 11.9 | 2000 | 30.3 |
| 41 | 47.4 | 14.6 | 14.4 | 3000 | 28.5 |
| 42 | 35.8 | 26.8 | 4.4 | 3000 | 10.7 |
| 43 | 34.0 | 0 | 3.5 | >10000 | 86 |
| 44 | 57.7 (70) | 15.6 | 10.5 | 2000 | 35.6 |
| 45 | 37.8 (>400) | 12.5 | 17.7 | 5000 | 30.8 |
| 46 | 43.4 (400) | 13.4 | 16.5 | 2000 | 34.5 |
| 47 | 20.9 | 13.1 | 18.3 |  | 15.6 |
| 48 | 26.0 | 12.5 | 20.5 |  | 18.3 |
| 49 | 10.7 | 18.2 | 28.5 | 8000 | 13.4 |
| 50 | 25.5 | 16.4 | 8.7 | >10000 | 28.3 |
| 51 | 24.6 | 18.3 | 9.5 |  | 13.5 |
| 52 | 25.5 | 12.5 | 6.8 |  | 10.1 |
| 53 | 20.3 | 14.2 | 10.1 |  | 19.2 |
| 54 | 25.5 | 11.3 | 15.4 |  | 20.3 |
| 55 | 29.0 | 15.8 | 23.3 |  | 16.4 |
| 56 | 14.9 | 20.5 | 20.3 | 10000 | 15.1 |
| 57 | 16.1 | 10.3 | 12.5 |  | 6.5 |
| 58 | 15.3 | 19.8 | 20.1 |  | 14.6 |
| 59 | 20.7 | 22.8 | 25.6 |  | 14.1 |
| 60 | 13.2 | 6.3 | 4.0 |  | 12.3 |
| 61 | 16.7 | 15.1 | 15.8 |  | 8.5 |
| 62 | 12.5 | 10.2 | 12.3 |  | 7.8 |
| 63 | 11.8 | 8.2 | 15.6 |  | 6.2 |
| 64 | 21.4 | 6.6 | 28.5 | 3000 | 15.9 |
| 65 | 17.3 | 10.9 | 21.0 |  | 19.2 |
| 66 | 34.4 | 15.7 | 20.7 | 2000 | 20.5 |
| 67 | 20.0 | 19.1 | 18.5 | 2000 | 17.3 |
| 68 | 17.6 | 5.8 | 16.5 |  | 20.3 |
| 69 | 12.0 | 6.7 | 13.5 |  | 12.7 |
| 70 | 23.2 | 7.0 | 17.2 |  | 10.0 |
| 71 | 20.0 | 9.2 | 19.5 |  | 11.4 |
| 72 | 29.9 | 23.4 | 28.7 | 1000 | 30.2 |
| 73 | 32.1 | 10.0 | 20.3 | 6000 | 28.8 |
| 74 | 30.2 | 24.2 | 18.5 | 5000 | 28.9 |
| 75 | 29.5 | 22.0 | 30.7 | 5000 | 29.2 |
| 76 | 15.7 | 13.9 | 16.2 | 2500 | 18.4 |
| 77 | 13.2 | 10.8 | 25.1 |  | 17.5 |
| 78 | 12.5 | 5.4 | 19.9 |  | 20.2 |
| 79 | 33.2 | 20.8 | 26.8 | 1000 | 31.5 |
| 80 | 31.9 | 16.2 | 30.3 |  | 28.5 |
| 81 | 15.3 | 17.6 | 18.3 |  | 20.3 |
| 82 | 23.8 | 13.5 | 20.5 |  | 30.1 |
| 83 | 20.0 | 12.1 | 27.6 |  | 19.3 |
| 84 | 28.4 | 15.3 | 8.6 | 10000 | 16.0 |
| 85 | 18.7 | 10.2 | 18.7 |  | 16.2 |
| 86 | 17.7 | 8.3 | 28.3 |  | 35.6 |
| 87 | 18.7 | 11.2 | 30.1 |  | 25.8 |
| 88 | 21.6 | 5.6 | 24.5 |  | 29.3 |
| 89 | 27.6 | 4.3 | 22.6 | 10000 | 13.2 |
| 90 | 19.7 | 13.7 | 10.8 |  | 15.0 |
| 91 | 21.4 | 15.2 | 14.7 |  | 31.0 |
| 92 | 10.0 | 11.1 | 8.9 |  | 20.3 |
| 93 | 20.4 | 14.7 | 24.4 |  | 26.8 |
| 94 | 26.6 | 15.8 | 27.9 | 500 | 37.4 |
| 95 | 17.1 | 14.5 | 30.0 |  | 32.3 |
| 96 | 26.1 | 18.9 | 28.5 |  | 36.7 |
| 97 | 13.0 | 14.7 | 26.8 |  | 37.3 |
| 98 | 31.9 | 16.4 | 28.3 | 4000 | 35.4 |
| 99 | 34.1 | 15.5 | 29.5 | 5000 | 30.3 |
| 100 | 14.0 | 10.0 | 22.4 |  | 27.6 |
| 101 | 23.1 | 18.3 | 27.9 |  | 31.4 |
| 102 | 22.4 | 15.2 | 30.4 |  | 29.7 |
| 103 | 29.7 | 14.2 | 29.5 | 500 | 35.8 |
| 104 | 27.4 | 13.2 | 25.3 | 3000 | 30.5 |
| 105 | 33.6 | 14.1 | 24.1 | 4000 | 31.4 |
| 106 | 26.4 | 7.3 | 20.3 | 1000 | 20.2 |
| 107 | 20.3 | 13.2 | 20.3 |  | 19.6 |
| 108 | 10.5 | 3.1 | 28.4 |  | 34.7 |
| 109 | 12.7 | 2.6 | 13.7 |  | 20.3 |
| 110 | 17.0 | 10.5 | 20.5 |  | 18.6 |
| 111 | 20.6 | 11.3 | 10.3 |  | 17.3 |
| 112 | 14.1 | 6.7 | 11.8 |  | 15.5 |
| 113 | 38.7 | 14.5 | 25.8 | 4000 | 30.4 |
| 114 | 33.2 | 18.3 | 26.8 | 2000 | 31.1 |
| 115 | 14.5 | 11.8 | 25.4 |  | 27.5 |

Table 2'

| Active ingredient No. | Anti-inf. | Acute toxicity |
|---|---|---|
| 116 | 59.8 | 4000 |
| 117 | 53.3 | 1500 |
| 118 | 32.7 | 2000 |
| 119 | 60.7 | 2000 |
| 120 | 38.3 | 750 |
| 121 | 64.5 | 3000 |
| 122 | 39.3 | 2000 |
| 123 | 38.3 | 1500 |
| 124 | 23.5 | 3000 |
| 125 | 18.1 | 1000 |
| 126 | 27.7 | 1000 |
| 127 | 58.8 | 5000 |
| 128 | 33.6 | 4000 |
| 129 | 38.6 | >10000 |
| 130 | 37.8 | 2000 |
| 131 | 33.6 | 2000 |
| 132 | 14.9 | 2000 |
| 133 | 38.3 | 2000 |
| 134 | 35.1 | 3000 |
| 135 | 37.2 | 1000 |
| 136 | 13.2 | 2000 |
| 137 | 16.7 | 2000 |
| 138 | 12.5 | 2500 |
| 139 | 11.7 | 1000 |
| 140 | 14.9 | 1000 |
| 141 | 13.8 | 2000 |
| 142 | 38.9 | 1500 |
| 143 | 45.4 | 1500 |
| 144 | 50.0 | 1500 |
| 145 | 60.2 | 2000 |
| 146 | 23.1 | 1000 |
| 147 | 20.4 | 1000 |
| 148 | 36.3 | 2000 |
| 149 | 42.2 | 500 |
| 150 | 14.0 | 2000 |
| 151 | 15.3 | 2500 |
| 152 | 22.6 | 1500 |
| 153 | 27.8 | 1500 |
| 154 | 29.0 | >10000 |
| 155 | 31.8 | >10000 |
| 156 | 43.0 | >10000 |
| 157 | 37.4 | >10000 |
| 158 | 32.7 | 2000 |
| 159 | 15.9 | 1000 |
| 160 | 10.8 | 2500 |
| 161 | 20.9 | 5000 |
| 162 | 13.0 | 1500 |
| 163 | 16.4 | 1500 |
| 164 | 29.0 | >10000 |
| 165 | 19.2 | 5000 |

Table 2'-continued

| Active ingredient No. | Anti-inf. | Acute toxicity |
|---|---|---|
| 166 | 21.5 | 5000 |

Chronic Inflammation (Adjuvant-Induced Arthritis)

The effects of 1 4-n-butyl benzophenone and 2 4-n-butyl-2'-fluorobenzophenone against adjuvant-induced arthritis were studied.

For the study, adult female rats of Sprague Drawley strain weighing approximately 200 g were used. All rats received 0.1 ml of a suspension of dry heat-killed tubercle bacilli (human strains, commercial product of Difco Co.) in liquid paraffin (5 mg/ml, w/v) by a single intradermal injection into the tail.

The treatment of the animals by the test compounds were started fourteen days after injection of the adjuvant when arthritis developed sufficiently accompanying edema and erythema in paws. Each compound was orally given to animals daily for ten days. Dosage levels employed were 50 an 100 mg/kg/day. Phenylbutazone was used as the reference drug.

Evaluations were made using the following parameters.

(1) Body weight gain
(2) Relative reduction in edema of the hind paws.

Results are summarized as follows:

Table 1

| Compounds | mg/kg | Body Weight Gain | | | |
|---|---|---|---|---|---|
| | | No. of rats | 0 | 6 | 10 days |
| | | | average | | |
| Positive Control | — | 8 | 202.0 | 195.9 | 194.6 |
| 4-n-butyl benzopheone | 100 | 6 | 229.2 | 217.5 | 218.2 |
| 4-n-butyl benzopheone | 200 | 7 | 214.1 | 213.3 | 220.1 |
| 4-n-butyl-2'-fluoro-benzophenone | 50 | 8 | 222.6 | 223.0 | 232.0 |
| 4-n-butyl-2'-fluoro-benzophenone | 100 | 10 | 211.8 | 205.8 | 214.4 |
| Phenylbutazone | 50 | 7 | 215.6 | 207.7 | 214.3 |

Table 2

| Compounds | mg/kg | Relative Change of Established Swelling in Hind Paws | | |
|---|---|---|---|---|
| | | No. of rats | Relative Volume Ratio of Swelling | |
| | | | 6 | 10 days |
| | | | average | |
| Positive Control | — | 8 | 1.43 | 1.42 |
| 4-n-butyl benzophenone | 100 | 6 | 0.97 | 1.02 |
| " | 200 | 7 | 0.76 | 0.75 |
| 4-n-butyl-2'-fluoro-benzophenone | 50 | 8 | 0.74 | 0.76 |
| " | 100 | 10 | 0.78 | 0.73 |
| Phenylbutazone | 50 | 7 | 0.75 | 0.75 |

No side effect considered to be related to the test compounds was seen during the study, while phenylbutazone caused the hemorrhage and the ulceration of stomach in most of the animals at dosage levels of 50 and 100 mg/kg/day.

What is claimed is:

1. A method for reducing chronic inflammation in a mammal, which comprises: administering to said mammal a therapeutically acceptable amount of 4-n-butyl-benzophenone.

* * * * *

UNITED STATES PATENT AND TRADEMARK OFFICE
CERTIFICATE OF CORRECTION

PATENT NO. : 4,145,444
DATED : March 20, 1979
INVENTOR(S) : YASUHIKO HAMAZAKI ET AL It is certified that error appears in the above-identified patent and that said Letters Patent are hereby corrected as shown below:

Please insert the following priority information:

[30] -- Jan. 1, 1976 [JP] Japan ... 51/232 -- rather than no priority data appearing in the Letters Patent.

Please insert the following inventors names:

[75] -- Koji Amemiya, Tokyo, Japan; and Katsumasa Saga, Ichikawa, Japan; --

Signed and Sealed this

Eighth Day of January 1980

[SEAL]

Attest:

SIDNEY A. DIAMOND

Attesting Officer — Commissioner of Patents and Trademarks